US00PP16412P2

(12) United States Plant Patent
Zaiger et al.

(10) Patent No.: US PP16,412 P2
(45) Date of Patent: Apr. 4, 2006

(54) INTERSPECIFIC TREE

(50) Latin Name: [***Prunus salicina*×(((*Prunus salicina*×(*Prunus salicina*×*Prunus armeniaca*))×(*Prunus salicina*×(*Prunus salicina*×*Prunus armeniaca*)))**]
Varietal Denomination: Dapple Supreme

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 162 days.

(21) Appl. No.: 10/983,281

(22) Filed: Nov. 8, 2004

(51) Int. Cl.
*A01H 5/00* (2006.01)

(52) U.S. Cl. ..... Plt./180

(58) Field of Classification Search ..... Plt./180
See application file for complete search history.

*Primary Examiner*—Anne Marie Grunberg

(57) ABSTRACT

A new and distinct variety of interspecific tree. The following features of the tree and its fruit are characterized with the tree budded on 'Citation' Rootstock (U.S. Plant Pat. No. 5,112), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of fruit.
2. Fruit with very good flavor and eating quality.
3. Fruit with an attractive red flesh color.
4. Relatively uniform size fruit throughout the tree.
5. Fruit holding firm on the tree 10 to 14 days after maturity (shipping ripe).

1 Drawing Sheet

Botanical classification: [*Prunus salicina*×(((*Prunus salicina*×(*Prunus salicina*×*Prunus armeniaca*))×(*Prunus salicina*×(*Prunus salicina*×*Prunus armeniaca*)))].

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree, consisting of various crosses between *Prunus salicina* and *Prunus armeniaca,* was originated and asexually reproduced by us in our experimental orchard located near Modesto, Stanislaus County, Calif.

Prior Varieties

Among the existing varieties of plum and interspecific trees, which are known to us, and mentioned herein, 'Mariposa' Plum (U.S. Plant Pat. No. 111), 'Red Beaut' Plum (U.S. Plant Pat. No. 2,539) and 'Flavor Queen' Interspecific (U.S. Plant Pat. No. 7,420).

Statement Regarding Federally Sponsored Research and Development

Not applicable.

Origin of the Variety

The present new variety of interspecific tree [Plum×((Plum×Plumcot)×(Plum×Plumcot))] was developed by us in our experimental orchard located near Modesto, Calif., as a first generation cross of two proprietary parents with field identification numbers 93LD115 and 64EG387. The maternal parent (93LD115) originated as a seedling from an open pollinated proprietary plum seedling of unknown parentage.

The paternal parent (64EG387) originated from crosses of the various parents 'Mariposa' Plum (U.S. Plant Pat. No. 111), 'Red Beaut' Plum (U.S. Plant Pat. No. 2,539) and apricots (*Prunus armeniaca*) of unknown parentages. In 1998 we budded a large number of these first generation seedlings to established trees of 'Citation' Rootstock (U.S. Plant Pat. No. 5,112) and under close and careful observation the present variety exhibited desirable tree and fruit characteristics and was selected for additional asexual propagation and commercialization.

Asexual Reproduction of the Variety

Asexual reproduction of the new and distinct variety of interspecific tree was by budding to 'Citation' Rootstock (U.S. Plant Pat. No. 5,112), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree is of large size, vigorous, upright growth, and a heavy and regular bearer of large size, clingstone fruit, nearly globose in shape, with an attractive, mottled red skin color. The flavor of the fruit is characterized by having a good balance between sugar and acid with very good flavor and eating quality with an average Brix of 14.9°. The fruit throughout the tree is relatively uniform in size and holds firm on the tree 10 to 14 days after maturity (shipping ripe). In comparison to the interspecific tree 'Flavor Queen' (U.S. Plant Pat. No. 7,420), the fruit of the new variety has mottled red skin color compared to yellow, having red flesh compared to yellow, is larger in size and approximately 30 days earlier in maturity.

In comparison to 'Red Beaut' Plum (U.S. Plant Pat. No. 2,539), the new variety has heavier, more consistent production, fruit with red flesh compared to yellow and is approximately 2 weeks later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 6 years of age, its flowers, foliage and fruit, as based on specimens grown near Modesto, Calif., with color in accordance with Munsell Book of Color.

Tree:

*Size.*—Large. Pruned to approximately 3 meters in height for economical harvesting of fruit.

*Vigor.*—Vigorous. Tree growth of approximately 1½ meters in the first growing season.

*Form.*—Upright, usually pruned to vase shape.

*Branching habit.*—Upright, crotch angle approximately 30°.

*Productivity.*—Productive. Thinning and spacing of fruit necessary for desirable market size fruit.

*Bearer.*—Regular. Adequate fruit set 4 consecutive years, no alternate bearing observed.

*Fertility.*—Self sterile, pollenizer required.

*Density.*—Medium dense. Usually pruned to vase shape to allow more sunlight to center of tree to improve fruit spur growth and fruit skin color.

*Hardiness.*—Hardy in all stone fruit growing areas of California. Winter chilling requirement approximately 500 hours at or below 45° F. Grown in USDA Hardiness Zone 9.

Trunk:

*Size.*—Large, stocky. Average circumference 46.8 cm measured at 29.3 cm above ground on a 6 year old tree.

*Texture.*—Medium shaggy, increases with age of tree.

*Color.*—Varies from 5Y 7/1 to 10Y 6/2.

Branches:

*Size.*—Medium. Average circumference 14.9 cm, measured at 1.2 meters above ground. Average crotch angle 30°, increases with heavy production of fruit.

*Surface texture.*—New growth relatively smooth, mature growth medium rough, roughness increases with age.

*Lenticels.*—Large. Average number 29 in a 25.8 square cm surface of branch. Average length 4.3 mm. Average width 1.4 mm. Color varies from 2.5YR 5/6 to 2.5YR 4/6.

*Color.*—New growth varies from 2.5GY 4/6 to 7.5R 3/6 where exposed to the sun. Old growth varies from 5YR 3/4 to 7.5YR 3/4, varies with age of growth.

Leaves:

*Size.*—Medium to large. Average length 114.7 mm. Average width 46.1 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentation over veins and midrib, glabrous. Lower surface relatively smooth except for small ridges created by midrib and pinnate venation, glabrous.

*Petiole.*—Medium length and width. Average length 17.5 mm. Average width 1.9 mm. Longitudinally grooved, glabrous. Color — lower surface 2.5GY 5/4. Upper surface 2.5R 4/4, varies with direct exposure to sunlight.

*Glands.*—Globose. Size — small. Average length 0.7 mm. Average diameter 0.4 mm. Number varies from 2 to 4, average number 2. Located primarily on base of leaf, upper portion of petiole. Color 2.5GY 4/4.

*Color.*—Upper surface varies from 5GY 3/4 to 2.5GY 4/4. Lower surface varies from 5GY 4/4 to 2.5GY 4/4. Midvein color varies from 5GY 5/4 to 2.5GY 6/4.

Flower buds:

*Size.*—Small to medium. Average length 8.1 mm. Average diameter 5.0 mm.

*Hardiness.*—Hardy in all stone fruit growing areas of California.

*Form.*—Conical.

*Pedicel.*—Average length 4.2 mm. Average width 0.6 mm. Color varies from 2.5GY 8/6 to 5GY 8/6.

*Color.*—N 9.5/.

*Number of buds per spur.*—Average number 5, varies from 3 to 7. Varies with age of spur.

Flowers:

*Size.*—Medium. Average height 11.0 mm. Average diameter 18.0 mm.

*Petals.*—Number 5, alternatively arranged to sepals. Size — medium. Average length 10.7 mm. Average width 8.3 mm. Form — obovate, apex rounded. Margin — sinuate. Both surfaces glabrous. Color — N 9.5/.

*Sepals.*—Number 5, alternately arranged to petals. Form — ovate, apex rounded. Margin — entire. Size — small. Average length 3.1 mm. Average width 2.6 mm. Both surfaces glabrous. Color — upper surface varies from 5GY 6/4 to 5GY 5/6. Lower surface varies from 5GY 8/6 to 5GY 7/8.

*Stamens.*—Average number per flower 27, varies from 25 to 28. Average filament length 7.4 mm. Filament color N 9.5/. Anther color varies from 5Y 9/6 to 5Y 8.5/10.

*Pollen.*—Self sterile, pollenizer required. Color varies from 5Y 8/8 to 5Y 7/8.

*Pistil.*—Normally one. Surface — glabrous. Average length 9.6 mm. Position of stigma — average of 0.8 mm above anthers. Color varies from 10Y 9/6 to 10Y 8/6.

*Fragrance.*—Moderate aroma.

*Blooming period.*—Date of First Bloom Feb. 13, 2004. Date of Petal Fall Feb. 23, 2004. Varies slightly with climatic conditions.

*Color.*—N 9.5/.

*Number flowers per flower bud.*—Average number 2, varies from 1 to 3.

*Pedicel.*—Average length 5.5 mm. Average width 0.6 mm. Color varies from 2.5GY 8/6 to 2.5GY 7/8. Surface — glabrous.

Fruit:

*Maturity when described.*—Firm ripe.

*Date of first picking.*—Jun. 19, 2004.

*Date of last picking.*—Jun. 25, 2004, varies slightly with climatic conditions.

*Size.*—Large. Average diameter axially 52.3 mm. Average transversely in suture plane 63.4 mm. Average weight 142.0 grams. Average weight varies slightly with fertility of the soil, amount of thinning and climatic conditions.

*Form.*—Globose.

*Suture.*—Shallow, extends from base to apex.

*Ventral surface.*—Slightly lipped.

*Apex.*—Usually slightly retuse.

*Base.*—Retuse.

*Cavity.*—Rounded to slightly elongated in suture plane. Average depth 5.5 mm. Average diameter 8.7 mm.

Stem:

*Size.*—Medium. Average length 10.6 mm. Average diameter 2.5 mm.

*Color.*—Varies from 7.5YR 5/6 to 7.5YR 4/6.

Flesh:

*Ripens.*—Evenly.

*Texture.*—Firm, meaty.

*Fibers.*—Few, small, tender.

*Firmness.*—Good, comparable to 'Flavor Queen' Interspecific (U.S. Plant Pat. No. 7,420).

*Aroma.*—Slight.

*Amydgalin.*—Undetected.

*Eating quality.*—Very good.

*Flavor.*—Very good, good balance between acid and sugar.

*Juice.*—Heavy, enhances flavor.

*Brix.*—Average 14.9°, varies slightly with amount of fruit per tree and climatic conditions.

*Color.*—Varies from 7.5R 4/10 to 5R 4/10. Pit cavity varies from 5R 3/8 to 5R 4/6.

Skin:

*Thickness.*—Medium.

*Surface.*—Smooth.

*Bloom.*—Moderate, complete coverage.

*Tendency to crack.*—Very slight.

*Color.*—Ground color varies from 5Y 7/6 to 7.5Y 6/4. Overspread with 7.5R 3/6 to 5R 3/6. Very small, randomly spaced areas of ground color exposed to skin surface giving a speckling pattern to skin.

*Tenacity.*—Tenacious to flesh.

*Astringency.*—Undetected.

Stone:

*Type.*—Clingstone.

*Size.*—Medium. Average length 21.8 mm. Average width 21.6 mm. Average thickness 13.7 mm.

*Form.*—Obovate.

*Base.*—Usually flat, varies from flat to rounded.

*Apex.*—Varies from rounded to slightly pointed. Average length 0.9 mm.

*Surface.*—Slightly pitted throughout, one long groove on each side of suture creating a narrow ridge running from base to apex.

*Sides.*—Unequal, with one side extending further from suture plane.

*Ridges.*—One on each side of suture, extending from base to apex. Few, small, short ridges running from base toward apex on some stones.

*Tendency to split.*—None.

*Color.*—Varies from 10YR 8/4 to 7.5YR 4/8.

Kernal:

*Size.*—Small. Average length 11.4 mm. Average width 9.1 mm. Average thickness 5.7 mm.

*Form.*—Ovate.

*Viability.*—Viable, embryo fully developed.

*Skin color.*—Varies from 10YR 7/8 to 10YR 5/10.

*Taste.*—Bitter.

Use: Dessert. Market — local and long distance.

Keeping quality: Good, held firm in cold storage 21 days at 38° to 42° F. without internal breakdown of flesh or appreciable loss of flavor.

Shipping quality: Good, minimal flesh bruising or skin scarring during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth, heavy production and regular bearing of attractive, large size fruit with very good flavor and eating quality; the fruit is further characterized by being relatively uniform in size throughout the tree and holding firm on the tree 10 to 14 days after maturity (shipping ripe).

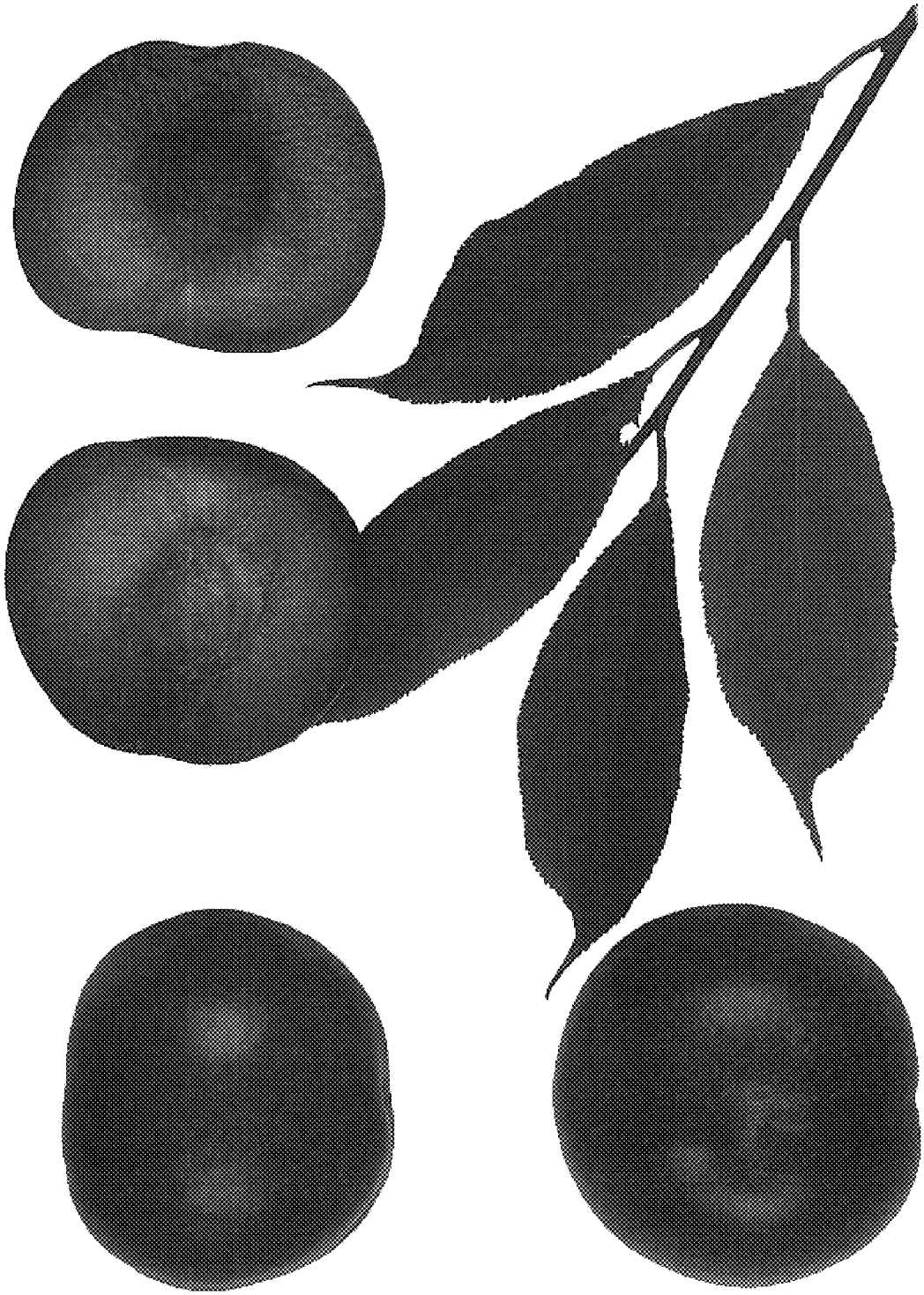

* * * * *